United States Patent [19]

Webb et al.

US005770700A

[11] Patent Number: 5,770,700
[45] Date of Patent: Jun. 23, 1998

[54] LIQUID FACTOR IX FORMULATIONS

[75] Inventors: Chandra Webb, Pelham, N.H.; Lawrence Bush, Tewksbury, Mass.

[73] Assignee: Genetics Institute, Inc., Cambridge, Mass.

[21] Appl. No.: 591,332

[22] Filed: Jan. 25, 1996

[51] Int. Cl.$^6$ .......................... A61K 47/00; A61K 38/48; A61K 38/36; A61K 47/26
[52] U.S. Cl. ........................ 530/383; 530/384; 514/12
[58] Field of Search .................. 514/8, 12; 530/383, 530/384

[56] References Cited

U.S. PATENT DOCUMENTS

| | | | |
|---|---|---|---|
| 4,405,603 | 9/1983 | Schwinn et al. | 424/101 |
| 4,470,968 | 9/1984 | Mitra et al. | 424/101 |
| 4,540,573 | 9/1985 | Neurath et al. | 424/85 |
| 4,597,966 | 7/1986 | Zolton et al. | 424/85 |
| 4,770,999 | 9/1988 | Kaufman et al. | 435/68 |
| 4,952,675 | 8/1990 | Mathews et al. | 530/383 |
| 5,288,853 | 2/1994 | Bhattacharya et al. | 530/383 |
| 5,457,181 | 10/1995 | Michalski et al. | 530/381 |
| 5,565,427 | 10/1996 | Freudenberg | 514/12 |

FOREIGN PATENT DOCUMENTS

| | | |
|---|---|---|
| 0 317 376 A | 5/1989 | European Pat. Off. . |
| 4001451 A1 | 8/1991 | Germany . |
| 90/02238 | 12/1990 | WIPO . |
| WO 95 26750 A | 10/1995 | WIPO . |
| WO 95 28954 | 11/1995 | WIPO . |

OTHER PUBLICATIONS

Miekka, et al., Blood 86 (10Sup1):73A (1995).
Rood, et al., Blood 86 (10Sup1):886A (1995).
MacLeod, et al., Scottish Nat Blood Transfusion Service, Research Disclosure 24427 (Aug. 1984).
Arakawa, Biopolymers 28:1397–1401 (1989).
Bajaj, et al., Prep. Biochem. 11(4):397–412 (1981).
Chen, et al., J. Pharm. Sci. 83(12):1657–1661 (1994).
Choo, et al., Nature 299:178–180 (1982).
Fair, et al., Blood 64(1):194–204 (1984).
Feldman, et al., Blood Coagulation and Fibrinolysis 5:939–948 (1994).
Freedman, et al., Biochemistry 34:12126–12137 (1995).
Freedman, et al., J. Biol. Chem. 270(14):7980–7987 (1995).
Gonzalez, et al., Vox Sang 68:1–4 (1995).
Hashimoto, et al., J. Biochem. 97:1347–1355 (1985).
Hrinda, et al., Seminars in Hematology, 28(3)Suppl 6:6–14 (1991).
Kurachi, et al., Proc. Natl. Acad. Sci., U.S.A. 79:6461–6464 (1982).
Liebman, et al., Proc. Natl. Acad. Sci., USA 82:3879–3883 (1985).
Manning, et al., Pharm. Res. 6(11):903–918 (1989).
Pittman, et al., Blood 79:389–397 (1992).
Rajeshwara, et al., Int. J. Peptide Protein Res. 44:435–440 (1994).
Rao, et al., Cell 82:131–141 (1995).
Soriano–Garcia, et al., Biochemistry 28:6805–6810 (1989).
Tharakan, et al., Journal of Chromatography 595:103–111 (1992).
Tsai, et al., Pharm. Res. 10(5):649–659 (1993).
Arakawa, et al., Pharm. Res. 8(3):285–291 (1991).
"Protein Structure, a practical approach", Ed. T.E. Creighton, IRL Press, Chap 14 (1989).
Pikal, Biopharm. 3(9):26–30 (1990).
Wang, et al., J. Parenteral Sci. and Tech. 42(2s):s3–s26 (1988).

Primary Examiner—Cecilia J. Tsang
Assistant Examiner—Michael Borin
Attorney, Agent, or Firm—M. C. Meinert; Thomas J. DesRosier

[57] ABSTRACT

Provided by the present invention are novel compositions and methods for obtaining concentrated preparations of factor IX and liquid formulations of factor IX suitable for storage and administration.

6 Claims, No Drawings

LIQUID FACTOR IX FORMULATIONS

FIELD OF INVENTION

The present invention relates generally to novel liquid formulations comprising factor IX.

BACKGROUND OF THE INVENTION

A variety of factors involved in the blood clotting process have been identified, including factor IX, a plasma glycoprotein. A deficiency of factor IX characterizes a type of hemophilia (type B). Treatment of this disease has traditionally involved intra venous infusion of human plasma-derived protein concentrates of factor IX. Infusion of blood concentrates involves the risk of transmission of various infectious agents, such as viral hepatitis and HIV, or thromboembolic factors. An alternative method of producing factor IX, by recombinant DNA techniques, has been described in U.S. Pat. No. 4,770,999, Kaufman et al., Sep. 13, 1988. The cDNA coding for human factor IX has been isolated, characterized, and cloned into expression vectors. See, for example, Choo et al., Nature 299:178–180 (1982); Fair et al., Blood 64:194–204 (1984); and Kurachi et al., Proc. Nat. Acad. Sci., U.S.A. 79:6461–6464 (1982). Thus, through advances in recombinant DNA technology, it has been possible to produce factor IX protein.

It is desirable to have both bulk and finished forms of factor IX, suitable for both storage and for delivery. Typically, a purification process for a protein results in concentrating the protein. This concentrated protein, also known as bulk protein, may be in a formulation buffer. Bulk protein, typically at a concentration of about 2 to at least 20 mg/mL, can, then be shipped frozen to a fill/finish facility where it is adjusted to an appropriate dosage concentration and placed into dosage vials or some device suitable for administration, e.g. a pre-fillable syringe. Ideally, the drug product is left in the liquid state and stored and administered as a liquid. Alternatively, the drug product is lyophilized, i.e., freeze-dried. Ideally lyophilized drug product has sufficient stability to be kept in long-term storage, i.e., greater than six months; lyophilized drug product is reconstituted at a later time by adding a suitable administration diluent just prior to patient use.

The decision to either maintain the finished drug product as a liquid or to freeze-dry it is usually based on the stability of the protein drug in those forms. Protein stability can be affected inter alia by such factors as ionic strength, pH, temperature, repeated cycles of freeze/thaw, and exposures to shear forces. Active protein may be lost as a result of physical instabilities, including denaturation and aggregation (both soluble and insoluble aggregate formation), as well as chemical instabilities, including, for example, hydrolysis, deamidation, and oxidation, to name just a few. For a general review of stability of protein pharmaceuticals, see, for example, Manning, et al., Pharmaceutical Research 6:903–918 (1989).

While the possible occurrence of protein instabilities is widely appreciated, it is impossible to predict particular instability problems of a particular protein. Any of these instabilities can result in the formation of a protein, protein by-product, or derivative having lowered activity, increased toxicity, and/or increased immunogenicity. Indeed, protein precipitation may lead to thrombosis, non-homogeneity of dosage form and amount, as well as clogged syringes. Also, specific to factor IX, there are several post-translational modifications (for example, the gamma carboxylation of certain glutamic acid residues in the N-terminus and the addition of carbohydrate) all of which provide potential sites that may be susceptible to modification upon storage. Thus, the safety and efficacy of any pharmaceutical formulation of a protein is directly related to its stability. Maintaining that stability in a liquid dosage form is generally different from a lyophilized dosage form because of greatly increased potential for molecular motion and therefore increased probability of molecular interactions.

When developing a liquid formulation, many factors are taken into consideration. Short-term, i.e., less than six months, liquid stability generally depends on avoiding gross structural changes, such as denaturation and aggregation. These processes are described in the literature for a number of proteins, and many examples of stabilizing agents exist ("Strategies to Suppress Aggregation of Recombinant Keratinocyte Growth Factor during Liquid Formulation Development", B. L. Chen et al., J. Pharm. Sci. 83(12):1657–1661, (1994); "Formulation Design of Acidic Fibroblast Growth Factor", P. K. Tsai et al., Pharm. Res. 10(5):649–659 (1993); "The Stabilization of Beta-Lactoglobulin by Glycine and NCl", Tsutomu Arakawa, Biopolymers 28:1397–1401 (1989); "Structural stability of lipase from wheat germ", A. N. Rajeshwara and V. Prakash, Internat. J. of Peptide & Prot. Res. 44:435–440 (1994); "Thermal Stability of Human Immunoglobulins with Sorbitol", M. Gonzalez et al., Vox Sang 68:1–4 (1995)). It is well known that an agent effective at stabilizing one protein actually acts to destabilize another. Once the protein has been stabilized against gross structural changes, developing a liquid formulation for long-term stability (greater than six months, for example) depends on further stabilizing the protein from types of degradation specific to that protein. More specific types of degradation may include, for example, disulfide bond scrambling, oxidation of oligosaccharides and/or certain residues, deamidation, cyclization, and the like. Although it is not always possible to pinpoint the individual degradation species, assays are developed to monitor subtle changes so as to monitor the ability of specific excipients to uniquely stabilize the protein of interest.

In addition to stability considerations, one generally selects excipients which will meet with the approval of various world-wide medical regulatory agencies. It is highly desirable that the formulation be approximately isotonic and that the pH of the formulation be in a physiologically suitable range upon injection/infusion, otherwise pain and discomfort for the patient may result. The choice and amount of buffer used is important to achieve the desired pH range. The choice and amount of agents used to modify tonicity is important to assure ease of administration.

Currently, there are only two commercially available (in the US), carrier-protein-free, plasma-derived factor IX formulations, both of which are freeze-dried products. Alpha Therapeutic Corporation provides lyophilized AlphaNine® SD, comprising heparin, dextrose, polysorbate 80, and tri (n-butyl) phosphate. This preparation is meant to be stored at temperatures between 2° and 8° C. Heparin is to be avoided as it is an anti-coagulant and tri(n-butyl) phosphate is irritating to mucous membranes; thus, this formulation is less than ideal. Armour Pharmaceutical Company provides lyophilized Mononine®, comprising histidine, sodium chloride and mannitol, is similarly meant to be stored at 2° to 8° C. The package insert recommends not storing this formulation for greater than one month at room temperature. There are no liquid formulated Factor IX products currently commercially available. Schwinn, PCT/EP90/02238, discloses factor IX, 0.9M saccharose, 0.5M lysine, and 0.003M calcium chloride, stored at 4°–8° C., stable for only a period of weeks and therefore, unsuitable for commercial production; this formulation is, unfortunately hypertonic and the pH is outside the range for comfortable administration, and therefore unsuitable for injection.

Ideally, formulations should provide for factor IX stability for greater than one year and for compatibility over a wide range of protein concentration (0.5 mg/mL to≧20 mg/mL, 125 U/mL to≧5000 U/mL for example). This allows for flexibility in methods of administration which may require high protein concentration, e.g., sub cutaneous administration, or low protein concentration, e.g. intra venous administration. Liquid formulations have many advantages over freeze-dried products with regard to ease of administration and use. Thus, there is a clear need for a liquid dosage form for Factor IX. Accordingly, there continues to exist a need in the art for methods for improving factor IX protein stability (and maintaining activity levels) and providing stable liquid formulations suitable for prolonged storage for greater than one year at 2 to 8° C.

BRIEF SUMMARY OF THE INVENTION

One aspect of the present invention provides novel compositions and methods for providing liquid preparations of factor IX useful as bulk protein. These compositions, either frozen or liquid, are stable for at least six months, and preferably up to 36 and 60 months; and can be stored at temperatures ranging from −100° C. to 40° C., from −80° C. to 0° C., and from −20° C. to 10° C. The compositions comprise factor IX, tonicity modifiers, cryoprotectants, and, optionally, a buffering agent and/or other excipients which further stabilize factor IX. The factor IX concentration ranges from about 0.1 to about 100 mg/mL (equivalent to about 20 to at least 20,000 U/mL), with 1 to 20 mg/mL (250 to 5000 U/mL) and 0.1 to 10 mg/mL (25 to 2500 U/mL) preferred. Tonicity modifiers include, but are not limited to, salts, sugars, polyols, and amino acids. Suitable amino acids include arginine and glycine at a concentration of about 25 to 500 mM, with about 40 to 300 mM and about 50 to 200 mM preferred. Suitable cryoprotectants include polyols, e.g. mannitol and sucrose, and range in concentration from about 1 to 400 mM, with about 5 to 200 mM and 20 to 100 mM preferred. Optionally, these bulk protein compositions may also contain a surfactant or detergent, such as polysorbate (e.g. Tween) or polyethyleneglycol (PEG), which may also serve as a cryoprotectant during freezing. The surfactant ranges from about 0.005 to 1%, with about 0.005 to 0.1% and about 0.005 to 0.02% preferred. Optionally, the composition may contain an appropriate buffering agent to maintain a physiologically suitable pH, e.g., in the range of about 5.8 to 8.0 with about 6.2 to 7.2 and about 6.5 to 7.0 being preferred. Buffering agents preferably include histidine, sodium citrate, potassium citrate, maleic acid, ammonium acetate, Tris, sodium phosphate, potassium phosphate, and diethanolamine, with sodium/potassium citrate preferred, with a preferred pH of about 6.5 to 7.5, and a concentration range of about 1–100 mM, with 5 to 50 mM and 10 to 25 mM preferred. Optionally, small amounts of a chelator such as EDTA are included, at a concentration of 0.05 to 50 mM, or 0.05 to 10 mM, or 0.1 to 5 mM, with about 1 to 5 mM preferred.

Another aspect of the present invention provides formulations of factor IX suitable for administration in a final dosage form, for example, via intra venous or sub cutaneous injection. Typically, large quantities of bulk drug are frozen and can be shipped, if necessary, to a manufacturing site where the bulk drug is filled into small vials; if desired, the final dosage form is a diluted, pH-adjusted form; bulk drug typically is a higher protein concentration than finished drug and does not need to be isotonic. The finished drug compositions comprise factor IX, tonicity modifiers, cryoprotectants and optionally a buffering agent and/or other excipients which further stabilize factor IX, as described, supra. The finished drug formulations are stable for at least six months and preferably up to 36 and 60 months; and can be stored at temperatures ranging from −100° C. to 40° C., from −20° C. to 37° C. and from 2° C. to 8° C. The concentrations of the excipients provide a combined osmolality of about 250 to 420 milliosmolal. Preferred formulations include Factor IX concentrations ranging from about 0.1 to at least 20 mg/mL (25 U/mL to 4000 U/mL); with sodium citrate as a buffering agent; some combination of mannitol, sucrose, arginine, and glycine as cryoprotectants and tonicity modifiers; and optionally small amounts of a chelator, such as EDTA (ca. 1 to 5 mM) and/or small amounts of polysorbate (0.005% to 0.02%).

DETAILED DESCRIPTION OF THE INVENTION

As used herein, factor IX includes both plasma derived and recombinantly or synthetically produced. Factor IX concentration is conveniently expressed as mg/mL or as U/mL, with 1 mg usually representing >150 U±100 U or more. One Unit of activity is defined as the amount of factor IX clotting activity in one milliliter of normal human plasma. The specific activity is the ratio of clotting activity concentration to protein concentration, expressed as U/mg of protein.

Amounts shown are understood to be ± about 10%, e.g., about 50 mM includes 50 mM±5 mM; e.g., 4% includes 4% ±0.4%, etc.

As used herein, the term "tonicity modifier" includes agents which contribute to the osmolality of the solution. Examples of tonicity modifiers include, but are not limited to, amino acids such as arginine, histidine, and glycine, salts such as sodium chloride, potassium chloride, and sodium citrate, and saccharides such as sucrose, glucose, and mannitol, and the like.

The term "cryoprotectant" generally includes agents which provide stability to the protein from freezing-induced stresses; however, cryoprotectants may also provide general stability, for example for bulk drug formulations during storage from non-freezing-induced stresses. Exemplary cryoprotectants include polyols, and saccharides such as mannitol and sucrose, as well as surfactants such as polysorbate, or polyethyleneglycol, and the like. While preferred concentrations of cryoprotectant range from about 0.2 to 4% (weight/volume), relatively high concentrations, for example greater than 5%, are also suitable; the levels used are limited only by those customarily used in clinical practice. The upper concentration limits for bulk drug may be higher than for finished dosage, e.g., greater than 5%. "Surfactants" generally include those agents which protect the protein from air/solution interface induced stresses and solution/surface induced stresses (e.g., resulting in protein aggregation), and may include detergents such as polysorbate-80 (Tween), for example, about 0.005 to 1% (volume/volume), or polyethyleneglycol (PEG), such as PEG8000, for example. Optionally, relatively high concentrations, e.g., up to 0.5%, are suitable for maintaining protein stability; however, the levels used in actual practice are customarily limited by clinical practice.

The term "buffering agent" encompasses those agents which maintain the solution pH in an acceptable range and may include histidine, phosphate (sodium or potassium), citrate (sodium or potassium), maleic acid, ammonium acetate, tris (tris (hydroxymethyl) aminomethane), diethanolamine, and the like. The upper concentration limits may be higher for bulk protein than for finished dosage protein forms as is readily appreciated by one skilled in the art. For example, while buffer concentrations can range from several millimolar up to the upper limit of their solubility, e.g., citrate, could be as high as 200 mM, one skilled in the art would also take into consideration both achieving and maintaining a physiologically appropriate concentration. Percentages are weight/volume when referring to solids dissolved in solution and volume/volume when referring to liquids mixed into solutions. For example, for sucrose, it is weight dry sucrose/volume of solution and for Tween, it is the volume of 100% stock/volume of solution. The term "isotonic with serum," 300±50 milliosmolal, is meant to be a measure of osmolality of the solution prior to administration. Maintaining physiological osmolality is important for the dosage formulations to be injectable without prior dilution. However, for bulk formulations, much higher osmolalities can be effectively utilized as long as the solution is made isotonic prior to use. The term "excipients" includes pharmaceutically acceptable reagents to provide appropriate tonicity, cryoprotection of the protein, maintenance of pH, and proper conformation of the protein during storage so that substantial retention of biological activity and protein stability is maintained.

The following examples illustrate practice of the invention. These examples are for illustrative purposes only and are not intended in any way to limit the scope of the invention claimed. Example 1 describes the effect of calcium addition and the effect of pH on clotting activity. Example 2 describes the effects of specific buffering agents on the formation of high molecular weight aggregates (HMW). Example 3 illustrates the use of the invention for higher concentrations of factor IX. Example 4 illustrates the complexity of excipient interactions in stabilizing factor IX. Example 5 describes factor IX in various formulations relating to freeze/thaw stability.

EXAMPLE 1

Effect of Calcium Ions

The preparation of recombinant factor IX has been described in U.S. Pat. No. 4,770,999, Kaufman, et al. One suitable purification method is that described in Hrinda, et al., Preclinical Studies of a Monoclonal Antibody—Purified Factor IX, Mononine™ Seminars in Hematology, 28(3):6 (July 1991). Other methods of preparation include the use of conformation-specific monoclonal antibodies as described by Tharakan, et al., "Physical and biochemical properties of five commercial resins for immunoaffinity purification of factor IX." Journal of Chromatography 595:103–111 (1992); and by Liebman, et al., "Immunoaffinity purification of factor IX (Christmas factor) by using conformation-specific antibodies directed against the factor IX-metal complex." Proc. Nat. Acad. Sci., USA 82:3879–3883 (1985); as well as conventional chromatographic procedures, for example, as described by Hashimoto, et al., "A Method for Systematic Purification from Bovine Plasma of Six Vitamin K-Dependent Coagulation Factors: Prothrombin, Factor X, Factor IX, Protein C, and Protein Z." J. Biochem. 97:1347–1355 (1985), and Bajaj, P. et al. Prep. Biochem. 11:397 (1981). "Large-scale preparation and biochemical characterization of a new high purity factor IX concentrate prepared by metal chelate affinity chromatography", P. A. Feldman et. al., Blood Coagulation and Fibrinolysis 5:939–948 (1994). Yet another method of purification is described in U.S. Ser. No. 08/472,823, filed Jun. 7, 1995; and incorporated herein by reference.

A well characterized property of factor IX is its ability to bind $Ca^{2+}$ ions. Structural studies indicate that $Ca^{2+}$ binding may confer a more stable structure, reducing the probability of molecular motion ("Structure of the Metal-free γ-Carboxyglutamic Acid-rich Membrane Binding Region of Factor IX by Two-dimensional NMR Spectroscopy", S. J. Freedman, B. C. Furie, B. Furie, and J. D. Baleja, J. Biol. Chem. 270(14):7980–7987 (1995); "Structure of the Calcium Ion-Bound γ-Carboxyglutamic Acid-Rich Domain of Factor IX," S. J. Freedman, B. C. Furie, B. Furie, and J. D. Baleja, Biochemistry 34:12126–12137 (1995); "The Structure of a $Ca^{2+}$-Binding Epidermal Growth Factor-like Domain: Its Role in Protein-Protein Interactions", S. Rao, P. Handford, M. Mayhew, V. Knott, G. Brownlee, and D. Stuart, Cell 82:131–141 (1995); "Structure of $Ca^{2+}$ Prothrombin Fragment 1 Including the Conformation of the Gla Domain", M. Soriano-Garcia, C. H. Park, A. Tulinsky, K. G. Ravichandran, and E. Skrzypczak-Jankun, Biochem. 28:6805–6810 (1989)). Presumably, less mobility accords a lower probability of molecular interaction, thereby reducing the probability of degrading processes. Surprisingly, this turns out not to be the case.

Samples are prepared in the formulations set forth in Table I below, at a recombinant factor IX protein concentration of ~0.5 mg/mil (100 U/ml) and an osmolality of 300±50 milliosmolal. All samples contain a recombinant form of factor IX. To examine the potential utility of $Ca^{2+}$ as a stabilizing agent, a set of samples was prepared in the formulations listed in Table 1. The formulation of sample A is the formulation used for commercially available plasma-derived lyophilized factor IX (Mononine™). All samples contain a recombinant form of factor IX.

TABLE 1

Sample Formulations

| Sample | pH Buffer (10 mM) | Salt (Tonicity Modifier) | Other Excipient |
|---|---|---|---|
| A | 7.0 histidine | 0.066 M NaCl (0.385%) | 165 mM mannitol |
| B | 7.0 histidine | 260 mM glycine | 29 mM sucrose |
| C | 7.0 histidine | 250 mM glycine, 5 mM $Ca^{2+}$ | 29 mM sucrose |
| D | 7.5 tris | 260 mM glycine | 29 mM sucrose |
| E | 7.5 tris | 250 mM glycine, 5 mM $Ca^{2+}$ | 29 mM sucrose |
| F | 7.5 diethanolamine | 260 mM glycine | 29 mM sucrose |
| G | 7.5 diethanolamine | 250 mM glycine, 5 mM $Ca^{2+}$ | 29 mM sucrose |

Samples of factor IX in each formulation were stored at 4° C. for 2.5 months. Samples were assayed for protein concentration and clotting activity. Factor IX activity is determined according to the method of Pittman, D., et al., Blood 79:389–397 (1992) utilizing factor IX-deficient blood. The ratio of clotting activity to protein concentration, the specific activity, expressed as Units/mg of protein, is given in Table 2. An acceptable specific activity would be no more than 20% greater than the starting specific activity.

TABLE 2

Factor IX Specific Activity

| Sample | time zero | 2.5 months |
|---|---|---|
| A | 219.9 | 161.3 |
| B | 191.8 | 153.2 |
| C | 239.4 | 964.1 |
| D | 209.3 | 135.8 |
| E | 212.1 | 1956.9 |
| F | 190.1 | 123.5 |
| G | 217.3 | 2570.8 |

The samples containing calcium, i.e., samples C, E, and G, have higher specific activities after 2.5 months of storage. This is due to the inclusion of $Ca^{2+}$ and indicates that the factor IX has undergone a conversion to an activated-like molecule. Activated Factor IX is Factor IX that has been cleaved at residues $R^{145}$–$A^{146}$ and $R^{180}$–$V^{181}$ and is then able to catalyze clotting. Normally, Factor IX circulates as intact protein and is not converted to its activated form unless there is initiation of the clotting cascade. Injecting someone with activated rhFIX could have thrombotic implications. Therefore inclusion of $Ca^{2+}$ at a concentration of 5 mM is destabilizing and is to be avoided.

EXAMPLE 2

Effects of Buffer Choice on HMW formation

The average specific activity after eight months of 4° C. storage of samples formulated in buffer/excipient combinations similar to and including those in Table 1, but without calcium, at pH 7.0 is 112.5±10.5 U/mg, but at pH 7.5 is only 84.0±22.1 U/mg, indicating subtle shifts in pH are significant for maintaining long-term factor IX stability.

Factor IX is prepared in a set of isotonic experimental formulations as summarized in Table 3, including several different excipient combinations for each buffering agent and some including less than 5 mM EDTA. Factor IX concentrations are approximately 1 mg/mL (average 161 U/mL). Samples are assayed for the amount of high molecular weight material (HMW) present and for clotting activity. The formation of significant (>3%) amounts of HMW is undesirable and as indicative of physical degradation of factor IX with possible impact on product safety and efficacy.

TABLE 3

Sample Formulations

| Buffering Agent (10–15 mM) | Excipients |
|---|---|
| Phosphate (either sodium or potassium phosphate, pH 7.0) | arginine-HCl, sodium chloride, glycine, sucrose, mannitol, glucose |
| Citrate (sodium, pH 6.0–6.5) | sorbitol, glucose, glycine, sucrose, arginine-HCl |
| Ammonium Acetate (pH 6.5–7.0) | mannose, mannitol, sodium chloride, arginine-HCl |
| Maleic Acid (pH 6.5) | glycine, mannose |

Table 4 shows the effects of the different buffering agents on HMW generation as measured by size exclusion chromatography (SEC-HPLC). Samples were stored at 30° C. for six weeks. Table 4 gives the average increase expressed as (HMW/total protein×100%) at six weeks minus that at time zero.

TABLE 4

Percent Increase HMW Generation

| Buffering Agent | Avg. Increase (% of total) |
|---|---|
| Phosphate: | 4.21 |
| Citrate: | 0.80 |
| Ammonium Acetate: | 3.42 |
| Maleic Acid: | 1.67 |

The citrate buffered samples had, on average, the smallest amount of HMW generated, regardless of the other excipients included. An appropriate buffer does not allow greater than a 2% increase.

All samples are stored further for six months at 4° C. and assayed for clotting activity. The average amount of activity remaining for samples containing the various saccharides varied greatly; sucrose-containing samples maintained an average 71% of the starting activity, mannitol 53%, glucose 52%, and mannose only 27%. Surprisingly, not all saccharides are equally effective at maintaining factor IX activity, despite the addition of other excipients.

EXAMPLE 3

Stability at high concentration

Another set of formulations is prepared comprising higher concentrations of factor IX; samples are prepared in the formulations listed in Table 5 at a concentration of 8 mg/mL (2000 U/mL). All contain 15 mM sodium citrate and are buffered at pH 6.8, without surfactant. BG4 is slightly hypertonic, the rest are isotonic.

TABLE 5

Sample Formulations

| BG1: | 2% sucrose, 2% arginine-HCl, 1 mM EDTA |
| BG2: | 4% sucrose, 1% glycine, 1 mM EDTA |
| BG3: | 15% arginine-HCl, 1% glycine |
| BG4: | 5% arginine-HCl, 1 mM EDTA |
| BG5: | 4% sucrose, 1% glycine |

Samples are stored in both glass vials and glass prefillable syringes for eight months at 4° C. to determine whether the amount of air/solution interface or siliconized stopper/solution interface would impact the stability of the product. No significant differences were seen by any stability indicating analytical methods between the vials and syringes. The results of several analytical methods are shown in Table 6. "Specific activity" and "HMW" have been described previously. "SDS-PAGE" is polyacrylamide gel electrophoresis; gels were scanned and bands quantified. Reversed phase HPLC is used to evaluate product heterogeneity and changes in peak ratios may indicate changes in the product, for example, oxidation of oligosaccharides.

TABLE 6

| Sample | Specific Activity, as % of control | HMW, as determined by SEC-HPLC | % full-length FIX, by SDS-PAGE | Reversed Phase HPLC ratio assay |
|---|---|---|---|---|
| BG-1 | 91% | 0.31 | 98.2 | 0.33 |
| BG-2 | 82% | 0.33 | 98.0 | 0.32 |
| BG-3 | 91% | 0.35 | 98.2 | 0.34 |

TABLE 6-continued

| Sample | Specific Activity, as % of control | HMW, as determined by SEC-HPLC | % full-length FIX, by SDS-PAGE | Reversed Phase HPLC ratio assay |
|---|---|---|---|---|
| BG-4 | 88% | 0.25 | 98.6 | 0.33 |
| BG-5 | 79% | 0.40 | 98.3 | 0.31 |
| control | 100% | 0.21 | 98.6 | 0.31 |

Even at the higher concentration of factor IX these formulations demonstrate feasibility of the invention.

EXAMPLE 4

Excipient Interactions

Another set of factor IX formulations, all containing citrate, is prepared as summarized in Table 7. All formulations are isotonic, contain factor IX at concentrations of 1 to 2 mg/mL (average 208 to 481 U/mL), use sodium citrate as the pH buffering agent, and are adjusted to pH 6.8.

TABLE 7

Sample Formulations

| Major Excipient (range of concentration, wt/vol %) | Used in combination with: |
|---|---|
| mannitol (55–275 mM, 1–5%) | arginine-HCl, EDTA, glycine, Tween-80, sucrose, NaCl, KCl |
| arginine-HCl (47–237 mM, 1–5%) | mannitol, EDTA, sucrose, glycine, Tween-80, glucose |
| glycine (66–306 mM, 0.5–2.3%) | mannitol, arginine-HCl, glucose, Tween-80, EDTA |
| sucrose (29–234 mM, 1–8%) | mannitol, arginine-HCl, glycine, NaCl, EDTA, Tween-80 |
| glucose (55–278 mM, 1–5%) | arginine-HCl, glycine, NaCl, KCl, EDTA |
| NaCl (100 mM, 0.58%) | sucrose, glucose, mannitol, EDTA |
| KCl (100 mM, 0.75%) | glucose, mannitol |

Samples are stored at 4° C. and assayed at several points in time. After eight months of 4° C. storage, nine samples maintain ~100% of the clotting activity of the starting material. The formulations of these nine are shown in Table 8 (all include 15 mM sodium citrate, are pH 6.8, and isotonic).

TABLE 8

| 1 | 4% sucrose, 1.4% glycine, 0.005% Tween-80 |
| 2 | 1% mannitol, 2% arginine-HCl, 0.5% glycine |
| 3 | 2.2% arginine-HCl, 0.75% glycine |
| 4 | 3% mannitol, 1% glycine |
| 5 | 3% mannitol, 1% glycine, 1 mM EDTA |
| 6 | 3% mannitol, 1.5% arginine, 0.005% Tween-80 |
| 7 | 3.3% arginine-HCl |
| 8 | 2% mannitol, 2% sucrose, 1.4% arginine |
| 9 | 4% sucrose, 1.4% glycine, 1 mM EDTA |

Several formulations containing similar excipients in similar ratios nevertheless, surprisingly, do not maintain clotting activity nearly as well.

Shown for these nine formulations are the results of other stability indicating assays. Specific activity is expressed as U/mg and an acceptable range is 250 to 275 U/mg. SEC-HMW is a measure of high molecular weight aggregates as determined by size-exclusion chromatography and the limit of acceptability is less than 1%. C-terminal clips is a measure of degradation species as determined by reversed phase chromatography and the limit of acceptability is less than 1%.

TABLE 9

| Sample | Recovery of Activity | Specific Activity | SEC HMW | C-Terminal Clips |
|---|---|---|---|---|
| 1 | ≧100% | 262 | 0.24% | 0.31% |
| 2 | ≧100% | 256 | 0.25% | 0.28% |
| 3 | ≧100% | 255 | 0.27% | 0.28% |
| 4 | ≧100% | 262 | 0.26% | 0.33% |
| 5 | ≧100% | 272 | 0.23% | 0.38% |
| 6 | ≧100% | 263 | 0.22% | 0.28% |
| 7 | ≧100% | 258 | 0.24% | 0.19% |
| 8 | ≧100% | 251 | 0.20% | 0.33% |
| 9 | ≧100% | 251 | 0.20% | 0.31% |

Based on the preferred formulations set forth in Tables 8 and 9, more preferred formulations include as follows: (all are buffered at pH 6.8 with citrate and are isotonic)

1) 3% mannitol, 1.5% arginine-HCl;
2) 3.3% sucrose, 1.5% glycine; and
3) 3.3% arginine-HCl

EXAMPLE 5

Effects of Freeze/Thaw Cycle

Ideally, a similar formulation is utilized for bulk protein as is used for the finished dosage form. This demands that the same formulation that stabilizes factor IX from long-term storage stresses also be appropriate for stabilizing factor IX from the stresses normally encountered by bulk protein, such as freezing and thawing.

Samples are prepared in the formulations set forth in Table 10 below, at a protein concentration of ~2 mg/mL (500 U/mL) and an osmolality of 300±50 milliosmolal. All include 10 mM sodium citrate, pH 6.8, and all are prepared both with and without 0.005% Tween-80 (polysorbate).

TABLE 10

Sample Formulations

| A. | 2.5% arginine-HCl, 2.2% sucrose |
| B. | 1.8% glycine, 2% sucrose |
| C. | 1.8% arginine-HCl, 2.4% mannitol |
| D. | 2.2% glycine, 0.2% mannitol |
| E. | 2.7% arginine-HCl, 0.8% mannitol |
| F. | 2% arginine-HCl, 2% sucrose, 0.9% mannitol |
| G. | 1.8% arginine-HCl, 2% mannitol, 0.8% sucrose |

Samples of factor IX in each formulation were subjected to five freeze-thaw cycles to determine susceptibility to freezing-induced denaturation, which can result in formation of protein aggregates. A series of freeze-thaw cycles is a useful indication of a protein's susceptibility to increased aggregate formation as may be observed during freezing and long-term storage. Samples are assayed for the amount of HMW present. Samples with and without Tween-80 (0.005%) have minimal aggregation (less than 0.15% HMW increase).

While the present invention has been described in terms of specific methods, formulations, and compositions, it is understood that variations and modifications will occur to those skilled in the art upon consideration of the present invention.

Numerous modifications and variations in the invention as described in the above illustrative examples are expected to occur to those skilled in the art and, consequently, only such limitations as appear in the appended claims should be placed thereon. Accordingly, it is intended in the appended claims to cover all such equivalent variations which come within the scope of the invention as claimed.

What is claimed:

1. A factor IX composition comprising about:
   65 to 235 mM arginine, and
   5 to 50 mM citrate.

2. A factor IX composition comprising about:
   65 to 235 mM arginine,
   0 to 60 mM sucrose, and
   5 to 50 mM citrate.

3. A factor IX composition comprising about:
   65 to 235 mM arginine,
   110 to 165 mM mannitol, and
   5 to 50 mM citrate.

4. A factor IX composition comprising about:
   155 to 235 mM arginine, and
   5 to 50 mM citrate.

5. A factor IX composition comprising about:
   95 to 119 mM arginine,
   58 to 73 mM sucrose, and
   15 mM citrate.

6. A factor IX composition comprising about:
   66 to 90 mM arginine,
   0 to 60 mM sucrose,
   110 to 165 mM mannitol, and
   5 to 50 mM citrate.

* * * * *